United States Patent [19]

Hogan

[11] Patent Number: 4,782,837

[45] Date of Patent: Nov. 8, 1988

[54] DENTAL ANALGESIA METHOD AND APPARATUS

[76] Inventor: Dennis E. Hogan, 6204 Belmore Ln., Hopkins, Minn. 55434

[21] Appl. No.: 855,633

[22] Filed: Apr. 25, 1986

[51] Int. Cl.$^4$ .............................................. A61N 1/34
[52] U.S. Cl. .................................. 128/421; 128/422; 128/419 R
[58] Field of Search ............... 128/421, 422, 419 R, 128/640

[56] References Cited

U.S. PATENT DOCUMENTS 4,676,257  6/1987  Halpren .................. 128/419 R

Primary Examiner—Lee S. Cohen
Assistant Examiner—Timothy Keegan
Attorney, Agent, or Firm—Lawrence M. Nawrocki

[57] ABSTRACT

A device for anesthetizing a patient (12) during normally painful medical procedures, such as various dental treatments, performed in the area of the patient's jaw and mouth regions. A TENS apparatus (10) having a hand control device (34) comprises the apparatus invention and is employed in practicing the method. The apparatus includes a slide control bar (36) which can be operated by the patient (12) to vary the amount of current being generated by the TENS apparatus (10). The attending dentist can utilize adjustable stops (38) for regulating the range of current flow which the patient (12) can induce. Further, the apparatus (10) employs uniquely designed electrodes (18, 18') for attachment to the hand (20) and face (22), respectively, of the patient (12). The facially applied electrode (18') is affixed externally to afford an accessible work path to the attending dentist.

4 Claims, 1 Drawing Sheet

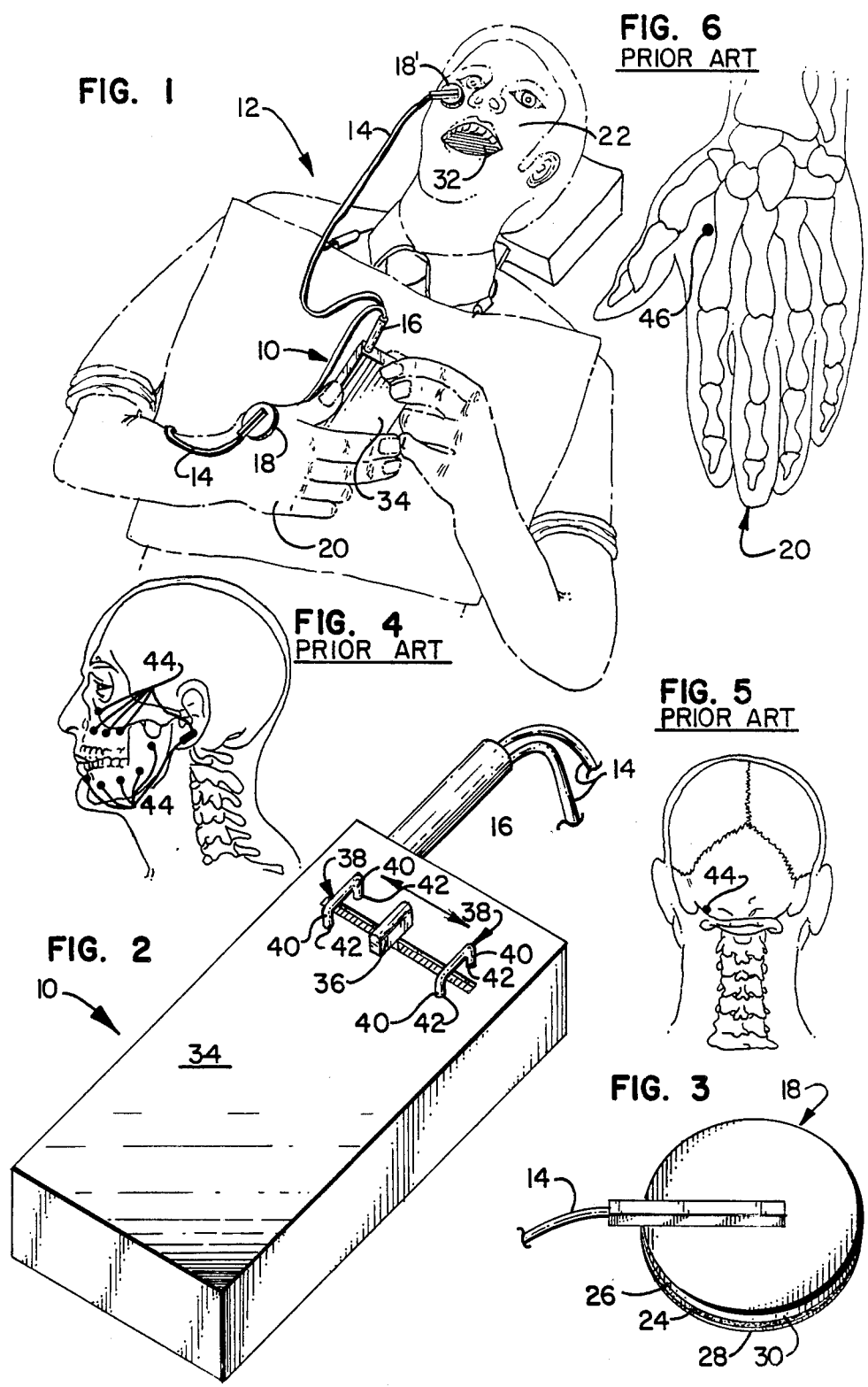

DENTAL ANALGESIA METHOD AND APPARATUS

TECHNICAL FIELD

The present invention is related generally to the field of analgesia. More narrowly, the invention is directed to dental analgesia or the relief of pain during dental procedures. The invention specifically deals with use of electrical stimulation as non-drug means for providing relief from pain during dental procedures.

BACKGROUND OF THE INVENTION

It is known in the prior art to use non-drug means for the relief of pain during medical procedures and dental procedures. Sound stimulation and electrical stimulation of nerves have both been found to alleviate the perception of pain during invasive dental procedures. The precise mechanism of how and why these methods work is unknown. It is, however, an observable phenomenon that pain relief can be obtained by utilization of this nerve stimulation.

U.S. Pat. No. 4,550,733 (Liss et al) illustrates an apparatus and method for effecting analygesia. The electronic dental analgesia of that patent utilizes a transcutaneous electronic nerve stimulation apparatus, or TENS unit, to send electronic waves across the cells to supress perceived pain during trauma associated with dental procedures. The device of that patent requires the placement of several electrodes at the following locations: the gum adjacent the work area, the hand and a trapezius muscle of the patient's shoulder. The device of that patent requires the patient to have an electrode and electrode lead within his or her mouth and at least two additional electrodes elsewhere on his or her body. Additionally, the Liss patent illustrates a structure generally requiring two hands to operate the dial-controlled TENS unit.

The electrode of the Liss patent is connected through a lead to a connector terminal where the lead terminates in a wire broach that has a plurality of barbs projecting radially outward and canted therefrom. The barbed, wire broach is inserted into a cotton swab which is moistened to provide electrical conductivity between the patient's gum and the wire end. The cotton swab electrode is then inserted into the patient's mouth and placed in the immediate vicinity of the tooth to be effected. The electrode, by being placed between the patient's cheek and gum, or lip and gum is retained generally in close proximity to the tooth to be affected. The dentist must then work around this cotton swab electrode and the associated electrode lead.

The present invention addresses these and other problems associated with prior art devices and provides for a new and improved method and apparatus for the alleviation of discomfort during dental procedures.

SUMMARY OF THE INVENTION

The present invention is a method employable to anesthetize regions of the jaw and mouth areas of a patient on whom normally painful medical procedures are to be performed. The method includes a step of providing an electrical nerve stimulation mechanism. Such a mechanism includes a pair of electrodes. In accordance with the method, a first of the electrodes is applied at a nerve location, previously ascertained, on the individual's hand, for example, by use of a device such as a neuro-detector. Similarly, the second electrode is placed externally in the area of the patient's jaw or mouth where the procedure is to be performed at a known nerve location thereon. Anesthetization is, thereafter, effected by operating the electrical nerve stimulation mechanism to induce current flow.

The invention also encompasses apparatus for performing anesthetization operations for use in decreasing pain perceived by a patient during dental procedures. Various types of electronic devices designed to accomplish this function are known in the prior art.

In a preferred manner of practicing the invention, a TENS unit (transcutaneous electrical nerve stimulation unit) is employed to provide electrical stimulation to an electrode that is placed at an appropriate location on the dental patient's body. It is an object of the invention to provide unobtrusive electrodes that may be precisely placed to alleviate pain and through which current flow may be regulated by the patient himself.

The preferred embodiment anticipates employment of disposable electrodes made of a variety of materials. The electrodes are placed on the patient's hand and face at sites to affect the appropriate nerves. The amount of stimulation received through the electrodes to the nerves is controlled by means of a unit held by the patient. The amount of this electrical stimulation can be limited by the addition of stops that can be set on the hand control unit by the attending dentist at maximum and minimum levels appropriate to fit the needs of the individual patient.

The appropriate nerves to be affected are located by means of, for example, a neuro-detector. The dentist marks these locations and places the electrodes thereon. The electrodes are placed on the hand and face by peeling off a paper backing on a preferrably sponge or foam core electrode exposing a karaya gum conductive adhesive for affixing the electrodes to the patient's skin.

The present invention is thus an electronic pain supression method and apparatus which can be applied to virtually any medical procedure, but especially those dental in nature. Because it effects pain supression without the use of drugs, it can be used by patients who are allergic or otherwise opposed to the use of routine analgesic drugs. This invention can be used whenever the prolonged use of drug analgesics is dangerous, inconvenient, or otherwise contra-indicated.

BRIEF DESCRIPTION OF THE DRAWINGS

FIG. 1 is a perspective illustration of electrodes in place upon a patient's hand and face;

FIG. 2 is a perspective view of a hand-held control unit employed in practicing the present invention;

FIG. 3 is an enlarged perspective view of an electrode;

FIG. 4 is a side view of the human skull;

FIG. 5 is a posterior view of the human skull; and

FIG. 6 is a dorsal view of the human hand.

DETAILED DESCRIPTION OF THE INVENTION

Referring now to the drawing wherein like reference numerals denote like elements throughout the several views, FIG. 1 illustrates a dental analgesia apparatus 10 in accordance with the present invention as being employed by a patient 12 having a dental procedure such as a tooth being filled performed on him. As seen in that figure, a transcuaneous electronic stimulation unit (TENS unit) 10 is provided and is hand-held by the patient 12. Electronic leads 14 are connected to the TENS unit 10 by a jack 16 and terminate in electrodes 18 for placement on the patient's hand 20 and face 22. These electrodes 18, as best illustrated in FIG. 3, can be comprised of a sponge or foam core 24 sandwiched between a base member 26 and a paper backing 28. One side of the electrode 18 has an adhesive 30 applied to the core 24 and is exposed only after the paper backing 28 on that side is peeled away.

Electrodes 18 of different sizes and shapes are envisioned. Additionally, electrodes 18 of various materials such as, for example, rubber, while not employed by the preferred embodiment, are possible and certainly not meant to be excluded.

Additionally, various adhesives could be utilized with this invention. Adhesive applied at the time of electrode 18 placement would function with this apparatus 10, as would an adhesive lamina 30 carried by the electrode base member 26. One envisioned adhesive is a karaya gum conductive adhesive. The preferred embodiment includes disposable electrodes 18 so the sterilization of electrodes after use would be unnecessary.

Because the envisioned electrode has no barbs and is placed on the patient's face 22 rather than within his mouth 32, it is an electrode 18 less obtrusive than those known in the prior art, and allows the patient 12 to be more comfortable. Additionally, an accessible work path to the tooth being worked on is provided for the attending dentist.

The hand control device 34, illustrated in FIG. 2, utilizes a slide control bar 36 for patient ease in adjusting the amount of current flow and commensurate electrical stimulation transmitted through the TENS unit 10 and electrodes 18 to the anatomical region of the patient being worked on. The control 36 may be, therefore, operated with one hand, or, if desirable, as illustrated in FIG. 1, with two.

In addition to the slide control bar 36, bridges or stops 38 may also be placed on the hand control device 34 by the attending dentist to further limit the maximum and minimum level of stimulation available for the patient 12 to administer to himself. Employment of such a slide control bar 36 functions to allow variation of the current generated by the hand control device and transmitted, via the electronic leads 14 and electrodes 18, to the region of the patient 12 being anesthetized, by using the bridges or stops 38. The full amount of movement of the slide control bar 36 which would otherwise be available becomes limited to only that defined between the stops 38.

With different patients, different circumstances may dictate that the maximum and minimum currents which may be generated and, commensurately, the maximum and minimum levels of stimulation, be adjusted. If desirable, therefore, the locations of the bridges or stops 38 can be made adjustable. Any appropriate means for anchoring the stops 38 can be employed. One such anchoring method would utilize a press fit between arms 40 of the stops 38 and the apertures 42 in which they are received.

Placement of the electrodes 18 is determined on an individual patient basis by use of a neuro-detector (not shown) to pin-point the patient's specific nerve locations. Typical nerve locations 44, 46, as represented by acupuncture points, are illustrated in FIGS. 4, 5, and 6. Use of a neuro-detector, however, more precisely establishes the locations for a specific patient.

One electrode 18' employed by the hand control device 34 of the present invention is placed externally on the patient's face 22 in close proximity to the tooth to be affected by the dental procedure. An additional electrode 18 is placed on the patient's hand 20 at a nerve location 46, as represented by an acupuncture point, as seen in FIG. 6. Electrical stimulation is effected by current transmitted from the TENS unit 10, through the facial electrode 18', through the patient's body, and returned to the TENS unit 10 by way of the hand-positioned electrode 18.

As might be surmised, although a neuro-detector can function to relatively precisely identify the location of a nerve to be stimulated, since exact neuro-patterns vary from individual to individual, electrode 18 position adjustment can be necessary. The attending dentist can, prior to performing the procedure in question, experiment with various electrode position patterns in order to achieve the optimum pattern for effecting maximum anesthetization. Pain response in the patient 12 can, thereby, be minimized.

Other modifications of the invention will be apparent to those skilled in the art in light of the foregoing description. This description is intended to provide specific examples of individual embodiments which clearly disclose the present invention. Accordingly, the invention is not limited to these embodiments or the use of elements having the specific configurations and shapes as presented herein. All alternative modifications and variations of the present invention which follows in the spirit and broad scope of the appended claims are included.

What is claimed is:

1. A method for anesthetizing selected regions of the jaw and mouth areas of an individual under going normally painful medical procedures being performed in those regions, comprising the steps of:
    (a) providing an electrical nerve stimulation mechanism having a pair of electrodes;
    (b) applying a first of the electrodes at a known nerve location on the individual's hand;
    (c) applying a second of the electrodes externally at a known nerve location proximate the region where the medical procedure is being performed;
    (d) affording control of operation of the electrical nerve ·stimulation mechanism to the individual being anesthetized to regulate current flow induced thereby to effect anesthetization of the region; and
    (e) restricting control of the mechanism operation to a defined range of current flow generated by the mechanism by placing a stop on the mechanism proximate the unit's control means to limit the availability of current flow selections.

2. A method for anesthetizing selected regions of the jaw and mouth area of an individual undergoing normally painful medical procedures being performed in those regions, comprising the steps of:
    (a) providing an electrical nerve stimulation mechanism having a pair of electrodes;
    (b) applying a first of the electrodes at a known acupuncture location on the individual's hand;
    (c) applying a second of the electrodes externally at a known acupuncture location proximate the region where the medical procedure is being performed;
    (d) affording control of operation of the electrical nerve stimulation mechanism to the individual being anesthetized to regulate current flow induced thereby to effect anesthetization of the region; and (e) restricting control of the mechanism operation to a defined range of current flow generated by the mechanism by placing a stop on the mechanism proximate the unit's control means to limit the availability of current flow selections.

3. A method for reducing dental pain, comprising the steps of :

(a) providing a transcutaneous electrical nerve stimulation (TENS) unit;

(b) locating the appropriate nerves to be affected;

(c) providing disposable electrodes for use with the TENS unit;

(d) placing an electrode on each of the patient's hand and face at sites to affect the appropriate nerves;

(e) modifying the TENS unit to contain a slide bar control for use by the patient for controlling electrical stimulation through the electrodes to the nerves by regulation of the degree of current flow provided by the electrodes; and (f) providing a stop for placement on the modified TENS unit to limit movement of the slide bar control to allow the attending dentist to alter the range of available stimulation on the TENS unit.

4. The method of claim 3 wherein the step of placing electrodes on the patient's hand and face at sites to affect the appropriate nerves further includes the steps of:

(a) providing an electrode having a karaya gum adhesive applied thereto and a paper backing overlying the adhesive; and (b) pulling the paper backing off a pair of electrodes and affixing the electrodes on the patient's hand and face.

* * * * *